United States Patent
Hazebrouck et al.

(10) Patent No.: US 7,628,818 B2
(45) Date of Patent: Dec. 8, 2009

(54) FIXED-BEARING KNEE PROSTHESIS HAVING INTERCHANGEABLE COMPONENTS

(75) Inventors: Stephen A. Hazebrouck, Winona Lake, IN (US); Daren L. Deffenbaugh, Winona Lake, IN (US); Mark A. Heldreth, Mentone, IN (US); Jack T. Bryant, Warsaw, IN (US); Rusty T. Meier, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 138 days.

(21) Appl. No.: 11/863,318

(22) Filed: Sep. 28, 2007

(65) Prior Publication Data

US 2009/0088859 A1 Apr. 2, 2009

(51) Int. Cl.
*A61F 2/38* (2006.01)
(52) U.S. Cl. .................................. 623/20.14
(58) Field of Classification Search ............. 623/20.14, 623/20.15, 20.28, 20.29, 20.3, 20.31, 20.21, 623/20.26, 20.27
See application file for complete search history.

(56) References Cited

U.S. PATENT DOCUMENTS

| | | | |
|---|---|---|---|
| 4,257,129 A | | 3/1981 | Volz |
| 4,673,407 A | | 6/1987 | Martin |
| 4,714,474 A | * | 12/1987 | Brooks et al. ............. 623/20.33 |
| 4,795,468 A | | 1/1989 | Hodorek et al. |
| 4,822,362 A | * | 4/1989 | Walker et al. ............. 623/20.32 |
| 4,944,757 A | | 7/1990 | Martinez et al. |
| 5,080,675 A | * | 1/1992 | Lawes et al. ............. 623/20.33 |
| 5,171,283 A | * | 12/1992 | Pappas et al. ............. 623/20.29 |
| 5,271,737 A | | 12/1993 | Baldwin et al. |
| 5,344,460 A | | 9/1994 | Turanyi et al. |
| 5,370,699 A | | 12/1994 | Hood et al. |
| 5,387,240 A | * | 2/1995 | Pottenger et al. ......... 623/20.29 |
| 5,405,396 A | * | 4/1995 | Heldreth et al. .......... 623/20.32 |
| 5,413,604 A | | 5/1995 | Hodge |

(Continued)

FOREIGN PATENT DOCUMENTS

EP 0 495 340 12/1991

(Continued)

OTHER PUBLICATIONS

European Search Report for European Patent Application No. 08253140.1-2310, Dec. 23, 2008, 8 pgs.

(Continued)

*Primary Examiner*—Alvin J. Stewart
(74) *Attorney, Agent, or Firm*—Barnes & Thornburg LLP (57) ABSTRACT

A fixed-bearing prosthesis includes a femoral component having a medial condyle surface and a lateral condyle surface. The knee prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. A posterior buttress extends along a posterior section of the perimeter of the tray's platform, and an anterior buttress extends along an anterior section of the perimeter of the tray's platform. Differently-sized tibial trays are interchangeable with differently-sized bearings.

20 Claims, 5 Drawing Sheets

U.S. PATENT DOCUMENTS

| | | | |
|---|---|---|---|
| 5,480,446 A | | 1/1996 | Goodfellow et al. |
| 5,609,639 A | * | 3/1997 | Walker .................... 623/20.29 |
| 5,658,342 A | * | 8/1997 | Draganich et al. ....... 623/20.29 |
| 5,702,464 A | * | 12/1997 | Lackey et al. ............. 623/20.32 |
| 5,755,801 A | * | 5/1998 | Walker et al. ............ 623/20.21 |
| 5,824,103 A | * | 10/1998 | Williams .................. 623/20.32 |
| 5,871,545 A | * | 2/1999 | Goodfellow et al. ..... 623/20.28 |
| 5,871,546 A | * | 2/1999 | Colleran et al. .......... 623/20.28 |
| 5,879,394 A | * | 3/1999 | Ashby et al. ............. 623/20.33 |
| 5,957,979 A | * | 9/1999 | Beckman et al. ......... 623/20.33 |
| 5,964,808 A | | 10/1999 | Blaha et al. |
| 6,039,764 A | * | 3/2000 | Pottenger et al. ......... 623/20.32 |
| 6,068,658 A | * | 5/2000 | Insall et al. ................ 623/20.3 |
| 6,090,144 A | * | 7/2000 | Letot et al. ............... 623/20.34 |
| 6,126,692 A | * | 10/2000 | Robie et al. .............. 623/20.32 |
| 6,162,254 A | * | 12/2000 | Timoteo ................... 623/20.33 |
| 6,210,444 B1 | * | 4/2001 | Webster et al. ........... 623/20.33 |
| 6,210,445 B1 | * | 4/2001 | Zawadzki ................. 623/20.33 |
| 6,217,618 B1 | * | 4/2001 | Hileman ................... 623/20.33 |
| 6,238,434 B1 | * | 5/2001 | Pappas ..................... 623/20.29 |
| 6,299,646 B1 | * | 10/2001 | Chambat et al. ......... 623/20.33 |
| 6,319,283 B1 | * | 11/2001 | Insall et al. ............... 623/20.33 |
| 6,361,564 B1 | * | 3/2002 | Marceaux et al. ........ 623/20.33 |
| 6,379,388 B1 | * | 4/2002 | Ensign et al. ............. 623/20.34 |
| 6,443,991 B1 | * | 9/2002 | Running ................... 623/20.27 |
| 6,506,215 B1 | * | 1/2003 | Letot et al. ............... 623/20.29 |
| 6,623,526 B1 | * | 9/2003 | Lloyd ....................... 623/20.28 |
| 6,660,039 B1 | * | 12/2003 | Evans et al. .............. 623/20.29 |
| 6,869,448 B2 | | 3/2005 | Tuke et al. |
| 6,923,832 B1 | * | 8/2005 | Sharkey et al. ........... 623/20.34 |
| 6,972,039 B2 | * | 12/2005 | Metzger et al. ........... 623/20.29 |
| 6,986,791 B1 | * | 1/2006 | Metzger ................... 623/20.24 |
| 7,094,259 B2 | * | 8/2006 | Tarabichi ................. 623/20.14 |
| 7,101,401 B2 | * | 9/2006 | Brack ....................... 623/20.33 |
| 2004/0215345 A1 | | 10/2004 | Perrone, Jr. et al. |
| 2005/0021147 A1 | | 1/2005 | Tarabichi |
| 2005/0209702 A1 | * | 9/2005 | Todd et al. ................ 623/20.33 |
| 2006/0052875 A1 | * | 3/2006 | Bernero et al. ........... 623/20.33 |
| 2007/0203582 A1 | * | 8/2007 | Campbell ................ 623/20.34 |
| 2008/0091272 A1 | * | 4/2008 | Aram et al. ............... 623/20.34 |
| 2009/0082873 A1 | * | 3/2009 | Hazebrouck et al. ..... 623/20.32 |

FOREIGN PATENT DOCUMENTS

| | | |
|---|---|---|
| EP | 0636352 | 2/1995 |
| FR | 2 653 992 | 11/1989 |
| WO | 99/66864 | 12/1999 |

OTHER PUBLICATIONS

DePuy Inc., "AMK Total Knee System Product Brochure", 1996, 8 pages.

DePuy Orthopaedics, Inc., "AMK Total Knee System Legend II Surgical Technique", 1998, 30 pages.

* cited by examiner

FIXED-BEARING KNEE PROSTHESIS HAVING INTERCHANGEABLE COMPONENTS

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a knee replacement procedure, a tibial tray is implanted into the patient's tibia. A bearing is secured to the tibial tray. The condyle surfaces of a replacement femoral component bear against the tibial bearing.

One type of knee prosthesis is a fixed-bearing knee prosthesis. As its name suggests, the bearing of a fixed-bearing knee prosthesis does not move relative to the tibial tray. Fixed-bearing designs are commonly used when the condition of the patient's soft tissue (i.e., knee ligaments) does not allow for the use of a knee prosthesis having a mobile bearing.

The components of a fixed-bearing knee prosthesis are typically provided by the manufacturer in matching sizes. Specifically, most currently available fixed-bearing knee prostheses allow the surgeon to use a number of bearing sizes for a particular size of femoral component, but each bearing size is generally matched to a particular size of tibial tray.

SUMMARY

According to one aspect, a fixed-bearing knee prosthesis includes a femoral component having a medial condyle surface and a lateral condyle surface. The prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. The platform has a posterior buttress extending along a posterior section of a perimeter of the platform and extending upwardly from an upper surface of the platform. An anterior buttress extends along an anterior section of the perimeter of the platform and upwardly from the upper surface of the platform.

The posterior buttress is generally Y-shaped and has a first arm extending along a posterior edge of the platform and having a first undercut defined therein. A second arm extends along the posterior edge of the platform in a direction away from the first arm and has a second undercut defined therein. A third arm extends anteriorly away from the first arm and the second arm.

A first imaginary line extends along a lateral-most edge of the first arm, with a second imaginary line extending along a medial-most edge of the second arm and intersecting the first imaginary line to define an angle of intersection therebetween.

In some illustrative embodiments, the angle of intersection of the imaginary lines is between 45-145°. In some illustrative embodiments, the angle of intersection of the imaginary lines is between 60-120°. In a specific illustrative embodiment, the angle of intersection of the imaginary lines is approximately 90°.

In some illustrative embodiments, the anterior buttress is generally T-shaped. In such cases, the anterior buttress includes a first arm extending along an anterior edge of the platform with a first undercut defined therein, and a second arm extending along the anterior edge of the platform in a direction away from the first arm and with a second undercut defined therein. A third arm extends posteriorly away from the first arm and the second arm.

The third arm of the posterior buttress may be contiguous with the third arm of the anterior buttress.

The bearing may include a first posterior tab positioned in the first undercut defined in the first arm of the posterior buttress, a second posterior tab positioned in the second undercut defined in the second arm of the posterior buttress, a first anterior tab positioned in the first undercut defined in the first arm of the anterior buttress, and a second anterior tab positioned in the second undercut defined in the second arm of the anterior buttress.

Both the medial bearing surface and the lateral bearing surface are defined in the upper surface of the bearing. The lower surface of the bearing contacts the upper surface of the platform and includes a posterior recess and an anterior recess formed therein. The posterior buttress is positioned in the posterior recess and the anterior buttress is positioned in the anterior recess. The posterior recess may be contiguous with the anterior recess.

According to another aspect, a fixed-bearing knee prosthesis includes a femoral component having a medial condyle surface and a lateral condyle surface. The prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. The platform has a posterior buttress extending along a posterior section of a perimeter of the platform and extending upwardly from an upper surface of the platform. An anterior buttress extends along an anterior section of the perimeter of the platform and upwardly from the upper surface of the platform.

The posterior buttress is generally Y-shaped and has a first arm extending along a posterior edge of the platform with a first undercut defined therein, and a second arm extending along the posterior edge of the platform in a direction away from the first arm with a second undercut defined therein. A third arm extends anteriorly away from the first arm and the second arm.

The anterior buttress includes a first arm extending along an anterior edge of the platform with a first undercut defined therein. A second arm of the anterior buttress extends along the anterior edge of the platform in a direction away from the first arm of the anterior buttress with a second undercut defined therein.

A first imaginary line extends along a posterior-most edge of the first arm of the anterior buttress and a posterior-most edge of the second arm of the anterior buttress. A second imaginary line extends along the longitudinal axis of the third arm of the posterior buttress and intersects the first imaginary line to define an angle of intersection therebetween. The angle of intersection is approximately 90°.

The anterior buttress may include a third arm extending posteriorly away from the first arm and the second arm in a direction parallel to the second imaginary line. The third arm of the posterior buttress may be contiguous with the third arm of the anterior buttress.

The bearing may include a first posterior tab positioned in the first undercut defined in the first arm of the posterior buttress, a second posterior tab positioned in the second undercut defined in the second arm of the posterior buttress, a first anterior tab positioned in the first undercut defined in the first arm of the anterior buttress, and a second anterior tab positioned in the second undercut defined in the second arm of the anterior buttress.

Both the medial bearing surface and the lateral bearing surface are defined in the upper surface of the bearing. The lower surface of the bearing contacts the upper surface of the platform and includes a posterior recess and an anterior recess formed therein. The posterior buttress is positioned in the posterior recess and the anterior buttress is positioned in the anterior recess. The posterior recess may be contiguous with the anterior recess.

According to another aspect, a fixed-bearing knee prosthesis includes a femoral component having a medial condyle surface and a lateral condyle surface, and a tibial tray having a platform with an elongated stem extending downwardly from a lower surface thereof. The platform has a generally Y-shaped posterior buttress extending upwardly from an upper surface of the platform. A pair of arms of the posterior buttress extend along a posterior section of a perimeter of the platform. Each of the pair of arms has an undercut defined therein. The platform also has an anterior buttress extending along an anterior section of the perimeter of the platform and extending upwardly from the upper surface of the platform. The knee prosthesis also includes a plurality of bearings configured to be secured to the tibial tray. Each of the plurality of bearings has a width that is different from at least some of the other of the plurality of bearings. Each of the plurality of bearings also has an upper surface having a medial bearing surface configured to articulate with the medial condyle surface of the femoral component and a lateral bearing surface configured to articulate with the lateral condyle surface of the femoral component. A lower surface of each of the plurality of bearings has at least one recess defined therein to receive the posterior buttress and the anterior buttress. Each of the plurality of bearings also includes a pair of posterior tabs arranged to be respectively received in the undercuts defined in the pair of arms of the posterior buttress.

The recess of the bearing may define a single, contiguous recess that receives both the posterior buttress and the anterior buttress.

The anterior buttress may be generally T-shaped with a pair of arms extending along an anterior edge of the platform. Each of the pair of arms of the anterior buttress may have an undercut defined therein. Each of the plurality of bearings may further include a pair of anterior tabs arranged to be respectively received in the undercuts defined in the pair of arms of the anterior buttress.

The posterior buttress may be contiguous with the anterior buttress.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-4, there is shown a fixed-bearing knee prosthesis 10. The knee prosthesis 10 includes a femoral component 12, a tibial tray 14, and a bearing 16. The tibial tray 14 includes a platform 18 having a fixation member, such as an elongated stem 20, extending away from its lower surface 22. The elongated tibial stem 20 is configured to be implanted into a surgically prepared end of a patient's tibia (not shown). It should be appreciated that other fixation members, such as one or more short pegs or posts, may be used in lieu of the elongated stem 20. The bearing 16 is securable to the tibial tray 14. In particular, as will be discussed below in greater detail, the bearing 16 may be snap-fit to the tibial tray 14. In such a way, the bearing 16 is fixed relative to the tibial tray 14 (i.e., it is not rotatable or moveable in the anterior/posterior or medial/lateral directions).

Figure 1:
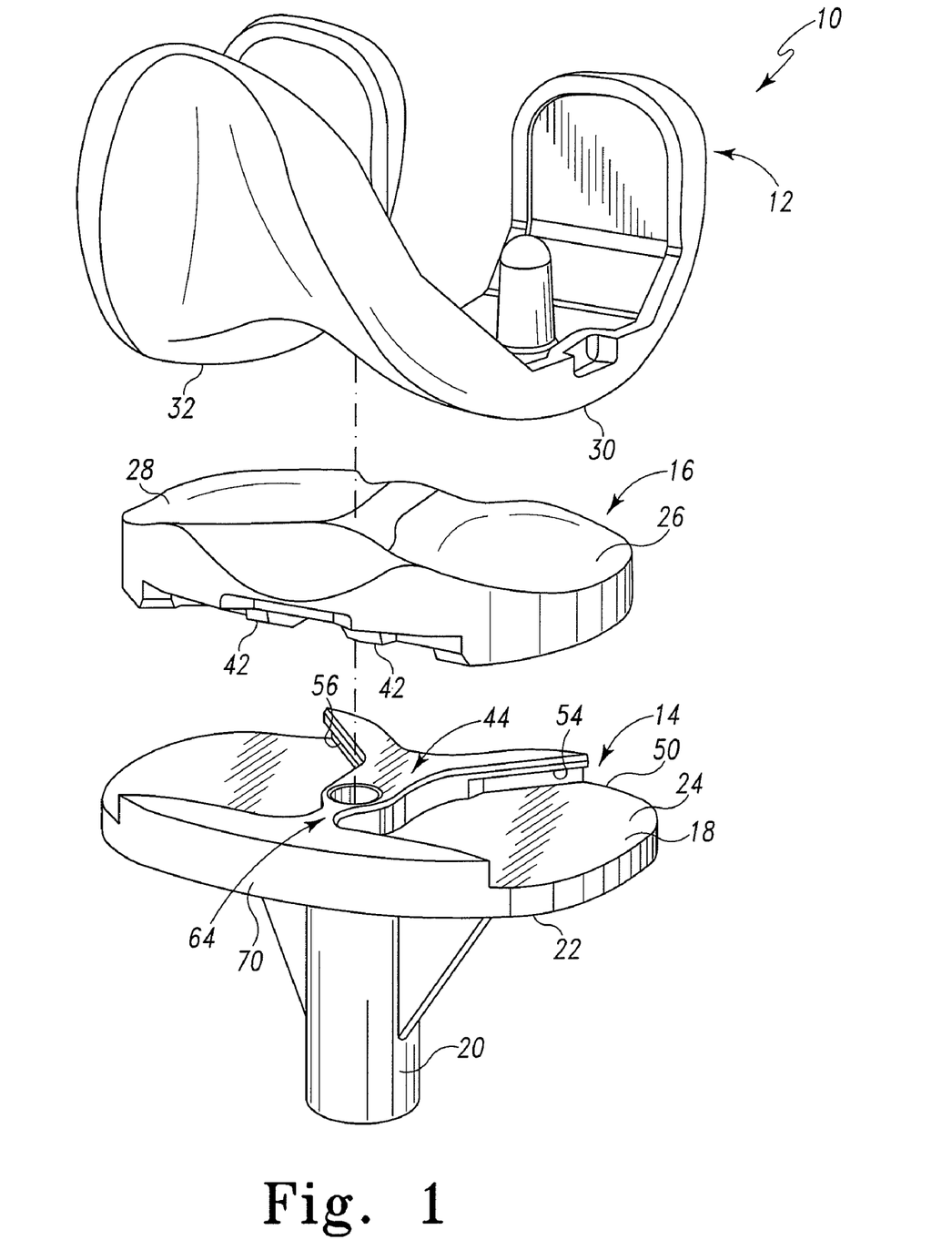
FIG. 1 is an exploded perspective view of a fixed-bearing knee prosthesis.

The bearing 16 includes a lateral bearing surface 26 and a medial bearing surface 28. The bearing surfaces 26, 28 are configured to articulate with a lateral condyle surface 30 and a medial condyle surface 32, respectively, of the femoral component 12. Specifically, the femoral component 12 is configured to be implanted into a surgically prepared end of the patient's femur (not shown), and is configured to emulate the configuration of the patient's natural femoral condyles. As such, the lateral condyle surface 30 and the medial condyle surface 32 are configured (e.g., curved) in a manner which mimics the condyles of the natural femur. The lateral condyle surface 30 and the medial condyle surface 32 are spaced apart from one another thereby defining an intercondylar notch therebetween.

The components of the knee prosthesis 10 that engage the natural bone, such as the femoral component 12 and the tibial tray 14, may be constructed with a biocompatible metal, such as a cobalt chrome alloy, although other materials may also be used. The bone engaging surfaces of these components may be textured to facilitate cementing the component to the bone. Such surfaces may also be porous coated to promote bone ingrowth for permanent fixation.

The bearing 16 may be constructed with a material that allows for smooth articulation between the bearing 16 and the femoral component 12, such as a polymeric material. One such polymeric material is polyethylene such as ultrahigh molecular weight polyethylene (UHMWPE).

Figure 2:
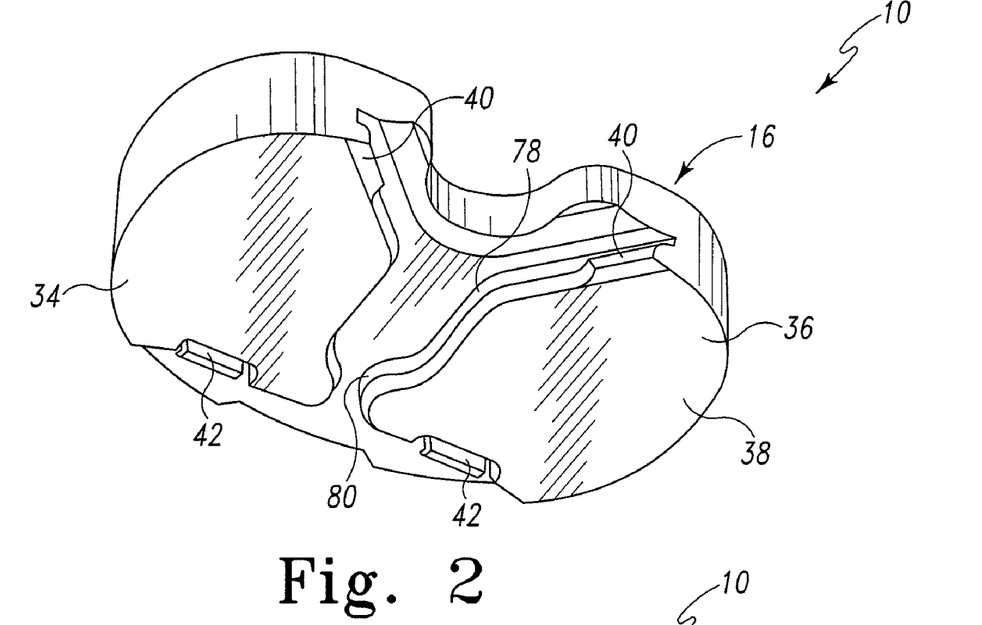
FIG. 2 is a bottom perspective view of the bearing of the knee prosthesis of FIG. 1.

As shown in FIG. 2, the lower surface 36 of the bearing 16 includes a lateral pedestal 34 and a medial pedestal 38. The pedestals 34, 38 have a number of posterior tabs 40 defined therein. A number of anterior tabs 42 are also defined in the bearing 16.

Figure 3:
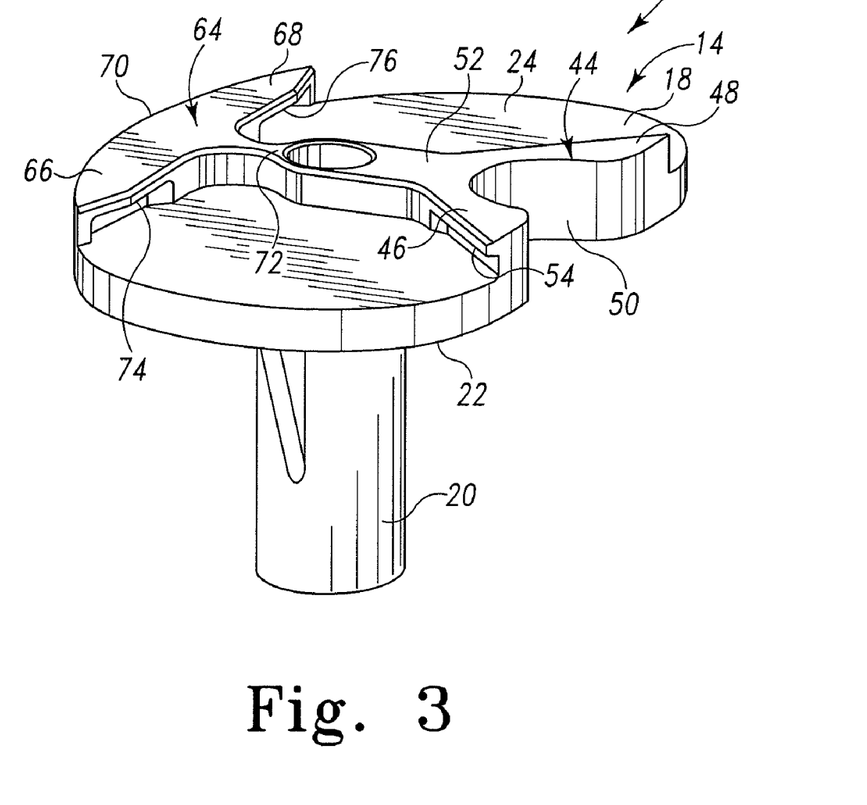
FIG. 3 is a perspective view of the tibial tray of the knee prosthesis of FIG. 1.
Figure 4:
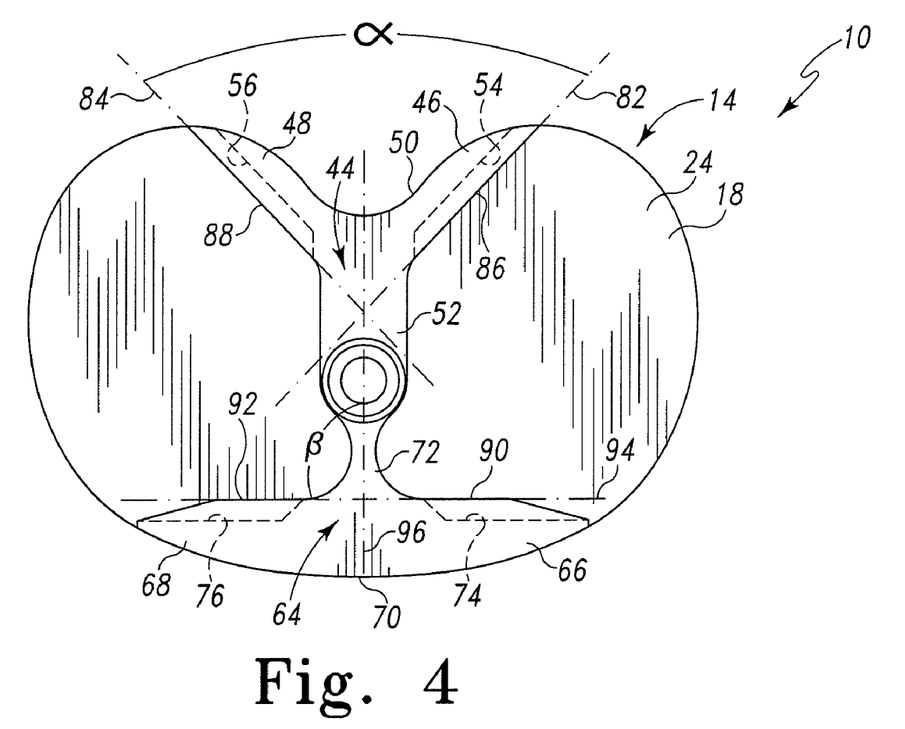
FIG. 4 is a plan view of the tibial tray of the knee prosthesis of FIG. 1.

As shown in FIGS. 3 and 4, a generally Y-shaped posterior buttress 44 extends upwardly from the upper surface 24 of the tibial tray 14. In the illustrative embodiment described herein, the posterior buttress 44 has a pair of arms 46, 48 extending along a posterior section of the perimeter of tibial tray's platform 18. Specifically, the lateral arm 46 of the posterior buttress 44 extends along the posterior edge 50 on the lateral side of the platform 18, whereas the medial arm 48 of the posterior buttress 44 extends along the posterior edge 50 on the medial side of the platform 18 in a direction away from the lateral arm 46. A third arm 52 of the posterior buttress 44 extends anteriorly away from the intersection of the lateral arm 46 and the medial arm 48 (i.e., in a direction toward the center of the platform 18).

The posterior buttress 44 has a pair of undercuts 54, 56 defined therein. Specifically, the lateral undercut 54 is defined in the lateral arm 46 of the posterior buttress 44, with the medial undercut 56 being defined in the medial arm 48 of the posterior buttress 44.

As also shown in FIGS. 3 and 4, a generally T-shaped anterior buttress 64 extends upwardly from the upper surface 24 of the tibial tray 14. In the illustrative embodiment described herein, the anterior buttress 64 has a pair of arms 66, 68 extending along an anterior section of the perimeter of tibial tray's platform 18. Specifically, the lateral arm 66 of the anterior buttress 64 extends along the anterior edge 70 on the lateral side of the platform 18, whereas the medial arm 68 of the anterior buttress 64 extends along the anterior edge 70 on the medial side of the platform 18 in a direction away from the lateral arm 66. A third arm 72 of the anterior buttress 64 extends posteriorly away from the intersection of the lateral arm 66 and the medial arm 68 (i.e., in a direction toward the center of the platform 18).

The anterior buttress 64 has a pair of undercuts 74, 76 defined therein. Specifically, the lateral undercut 74 is defined in the lateral arm 66 of the anterior buttress 64, with the medial undercut 76 being defined in the medial arm 68 of the anterior buttress 64.

In the illustrative embodiment of FIGS. 1-4, the posterior buttress 44 of the tibial tray 14 is contiguous with the tray's anterior buttress 64. Specifically, as shown in FIG. 4, the third arm 52 of the posterior buttress 44 is contiguous with the third arm 72 of the anterior buttress 64. However, as will be discussed below in greater detail, other embodiments are contemplated, including arrangements in which the buttresses are not contiguous. Moreover, the two buttresses 44, 64 are herein described as being of a similar height, although the buttresses could be embodied has having dissimilar heights.

To secure the tibial bearing 16 to the tibial tray 14, the posterior tabs 40 of the bearing 16 are positioned in the posterior undercuts 54, 56 of the tibial tray 14. Thereafter, the anterior portion of the tibial bearing 16 is advanced downwardly toward the tibial tray 14 such that the anterior tabs 42 of the tibial bearing 16 are deflected by the anterior buttress 64 and thereafter snapped into the anterior undercuts 74, 76 of the anterior buttress thereby securing the bearing 16 to the tray 14.

As the anterior portion of the bearing 16 is advanced downwardly in such a manner, the buttresses 44, 64 of the tibial tray 14 are captured between the pedestals 34, 38 of the bearing's lower surface 36. Specifically, the lower surface 36 of the bearing 16 has a posterior recess 78 and an anterior recess 80 defined therein. The posterior recess 78 is configured to compliment the shape of the posterior buttress 44 of the tibial tray 14. That is, when the bearing 16 is secured to the tibial tray 14, the sidewalls of the pedestals 34, 38 which define the posterior recess 78 contact the edges of the posterior buttress 44. Likewise, the anterior recess 80 is configured to compliment the shape of the anterior buttress 64 of the tibial tray 14—i.e., when the bearing 16 is secured to the tibial tray 14, the sidewalls of the pedestals 34, 38 which define the anterior recess 80 contact the edges of the anterior buttress 64. The dimensions of the recesses 78, 80 and the buttresses 44, 64 are selected such that a relatively tight fit is achieved. In such a way, the bearing 16 is fixed relative to the tibial tray 14. In particular, the configuration of the buttresses 44, 46 and the pedestals 34, 38 formed in the lower surface 36 of the bearing 16 prevent movement of the bearing 16 relative the tibial tray 14 in the anterior/posterior direction and the medial/lateral direction. Moreover, the posterior tabs positioned in the undercuts 54, 56 and the anterior tabs 42 positioned in the undercuts 74, 76 prevent lift off of the bearing 16 from the tibial tray 14. Rotational micromotion is reduced, if not prevented all together, by the relatively tight fit of the buttresses 44, 64 of the tibial tray 14 into the recesses 78, 80 of the bearing 16—particularly along the third arm 52 of the posterior buttress 44 and/or the third arm 72 of the anterior buttress 64.

As alluded to above, in the illustrative embodiment described herein, the posterior buttress 44 is embodied as a generally Y-shaped structure having a pair of arms 46, 48 extending in opposite directions along the posterior edge 50 of the tray's platform 18, with a third arm 52 extending anteriorly from the posterior edge 50 of the tibial tray 14 (i.e., in a direction toward the center of the tray's platform 18). As shown in FIG. 4, the lateral arm 46 of the posterior buttress 44 includes a lateral-most edge 86, whereas the medial arm 48 of the posterior buttress 44 has a medial-most edge 88. An imaginary line 82 extends along the lateral-most edge 86 and intersects an imaginary line 84 that extends along the medial-most edge 88 to define an angle of intersection ($\alpha$). In the exemplary embodiments described herein, the angle of intersection ($\alpha$) is between 45-145°. In more specific illustrative embodiments, the angle of intersection ($\alpha$) is between 60-120°. In one such specific illustrative embodiment, the angle of intersection ($\alpha$) is approximately 90°. Examples of such illustrative embodiments of the posterior buttress 44 are shown in FIGS. 6-9.

It should be appreciated that increasing the angle of intersection ($\alpha$) reduces micromotion, while decreasing the angle of intersection ($\alpha$) increases the load bearing surface area of the tibial tray 14. Although other configurations may be utilized, it has been found that arranging the arms 46, 48 of the posterior buttress 44 as described above (i.e., having an angle of intersection ($\alpha$) between 60-120°) provides an unexpectedly beneficial working balance between these two considerations. On particularly well-balanced arrangement of the posterior buttress 44 is found in the illustrative embodiment where the angle of intersection ($\alpha$) is approximately 90°.

As alluded to above, in the illustrative embodiment described herein, the anterior buttress 64 is embodied as a generally T-shaped structure having a pair of arms 66, 68 extending in opposite directions along the anterior edge 70 of the tray's platform 18, with a third arm 64 extending posteriorly from the anterior edge 70 of the tibial tray 14 (i.e., in a direction toward the center of the tray's platform 18). As shown in FIG. 4, the lateral arm 66 of the anterior buttress 64 includes a posterior-most edge 90, whereas the medial arm 68 of the anterior buttress 64 has a posterior-most edge 92. An imaginary line 94 extends along both the posterior-most edge 90 of the lateral arm 66 and the posterior-most edge 92 of the medial arm 68. An imaginary center line 96 extends along a longitudinal axis of the third arm 52 of the posterior buttress 44. As shown in FIG. 4, the imaginary center line 96 bisects the third arm 52 of the posterior buttress 44. The imaginary line 94 extending along the posterior-most edges 90, 92 of the arms 66, 68 of the anterior buttress 64 intersects the imaginary center line 96 extending along the longitudinal axis of the third arm 52 of the posterior buttress 44 to define an angle of intersection ($\beta$). In the illustrative embodiments described herein, the arms 66, 68 (and hence the undercuts 74, 76) of the anterior buttress 64 are configured to extend in the medial/lateral direction. As a result, in the illustrative embodiments described herein, the angle of intersection ($\beta$) is approximately 90°. As shown in FIGS. 6-9, such is the case throughout numerous illustrative embodiments of the anterior buttress 64.

Figure 5:
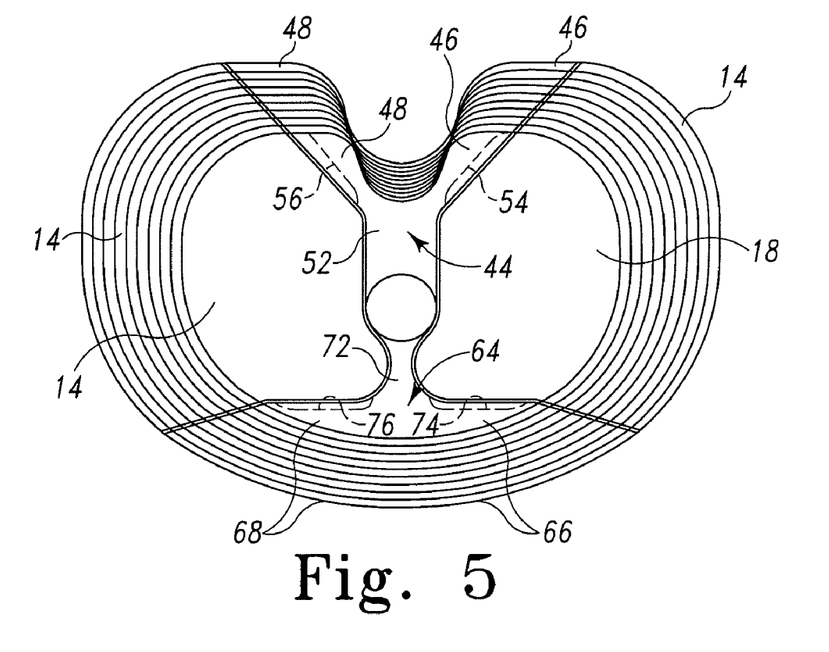
FIG. 5 is a diagrammatic plan view of a number of differently sized tibial trays of the knee prosthesis of FIG. 1.
Figure 6:
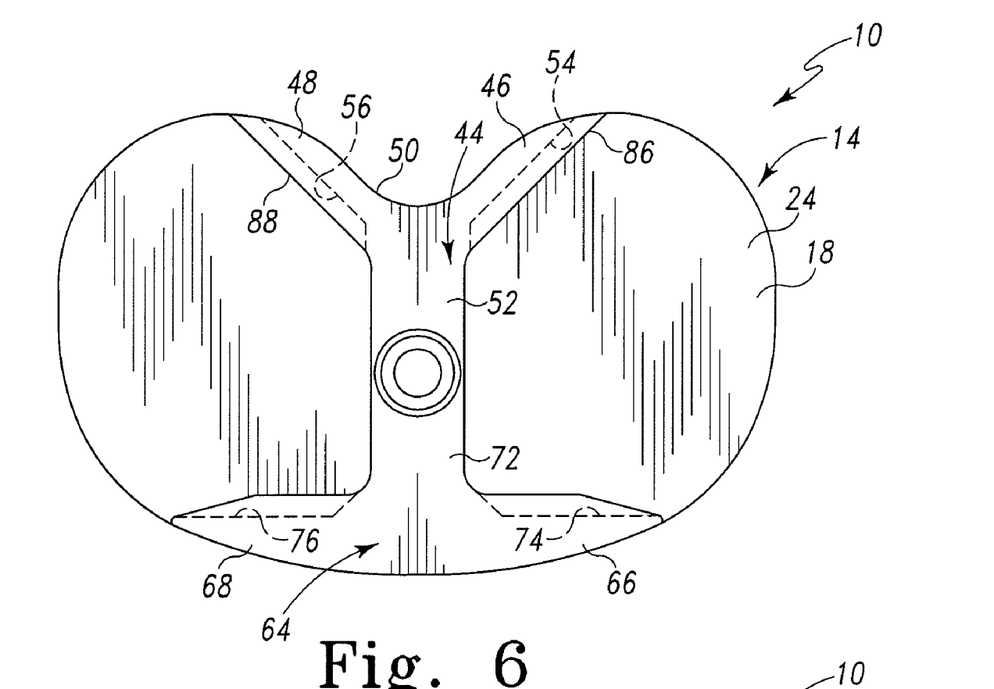
FIGS. 6-9 are similar to FIG. 4, but showing different embodiments of the tibial tray.

A given design of a fixed-bearing knee prosthesis is typically made commercially available in a variety of different sizes, particularly in a variety of different widths. This is done to accommodate the many variations in patient size and anatomy across a population. However, the configuration of the fixed-knee prosthesis 10 of the present disclosure allows for a high degree of flexibility in regard to the sizing of the tibial tray 14 and the bearing 16. In particular, FIG. 5 is a diagrammatic representation of a plurality of differently-sized tibial trays 14 superimposed upon one another. As can be seen, despite each of the individual trays 14 having a size (e.g., width) that is different from the other trays 14 of the group, the basic configuration of the posterior buttress 44 and the anterior buttress 64 remains the same across the range of differently-sized trays 14. Specifically, the location of the undercuts 54, 56 defined in posterior buttress 44, respectively, remains the same across the range of differently-sized trays 14. Even though the posterior undercuts 54, 56 remain in the same location across the range of differently-sized trays 14, the width of the arms 46, 48 is varied to accommodate the overall width of a given tray 14. In a similar manner, the location of the undercuts 74, 76 defined in anterior buttress 64, respectively, remains the same across the range of differently-sized trays 14, although the width of the arms 66, 68 is varied to accommodate the overall width of a given tray 14. As shown in FIG. 5, the size and configuration of the third arms 52, 72 of the posterior buttress 44 and the anterior buttress 64, respectively, remain unchanged across the range of differently-sized trays 14.

Differently-sized bearings 16 may also be configured in such a manner. In particular, a plurality of the bearings 16 may be designed with each of such a plurality of bearings 16 having a different size, particularly a different width. However, each of such differently-sized bearings 16 may include mating features that are commonly-sized and commonly-located with the commonly-sized and commonly-located features of the tibial tray 14 described above. In particular, each of the bearings 16 across a range of differently-sized bearings 16 may include a posterior recess 78 and an anterior recess 80 that is positioned and sized to tightly fit against the edges of the posterior buttress 44 and the anterior buttress 64, respectively, of each of the tibial trays 14 across the range of differently-sized trays 14.

The posterior tabs 40 are commonly-sized and commonly-located across the range of differently-sized bearings 16 so that they are positioned in the respective posterior undercuts 54, 56 of each of the tibial trays 14 across the range of differently-sized trays 14. Likewise, the anterior tabs 42 are commonly-sized and commonly-located across the range of differently-sized bearings 16 so that they are positioned in the respective anterior undercuts 74, 76 of each of the tibial trays 14 across the range of differently-sized trays 14.

It should be appreciated from the above-discussion that the general configuration of the buttresses 44, 64 (including contiguous variations thereof) is the same across the range of differently-sized tibial trays 14. Likewise, the general configuration of the recesses 78, 80 (including contiguous variations thereof) and the general configuration of tabs 40, 42 are the same across the range of differently-sized bearings 16. As such, any size bearing 16 may be secured to any size tibial tray 14. This provides the orthopaedic surgeon with greater flexibility of matching the knee prosthesis 10 to a particular patient's anatomy.

As shown in FIGS. 6-9, other configurations of the posterior buttress 44 and the anterior buttress 64 are also contemplated. For example, in the illustrative embodiment of FIG. 6, the third arm 52 of the posterior buttress 44 and the third arm 72 of the anterior buttress 64 are configured to define a contiguous structure having a substantially constant width throughout its entire length. It should be appreciated that the recesses 78, 80 defined in the lower surface 36 of the bearing 16 are likewise reshaped in the embodiment of FIG. 6 to accommodate the different shape of the buttresses 44, 64 of the tibial tray 14. In other words, while its contemplated that the design of the buttresses 44, 64 may be altered, it is also contemplated that the design of the recesses 78, 80 is altered accordingly to compliment the configuration of the buttresses 44, 64. It is also contemplated that the general configuration of the buttresses 44, 64 of FIG. 6, along with the corresponding configuration of the recesses 78, 80 and tabs 40, 42 of the complimentary bearing 16, may also remain the same across a range of differently-sized trays 14 and bearings 16 to accommodate the interchangeability of various sizes of trays and bearings in a similar manner to as described above in regard to FIG. 5.

Figure 7:
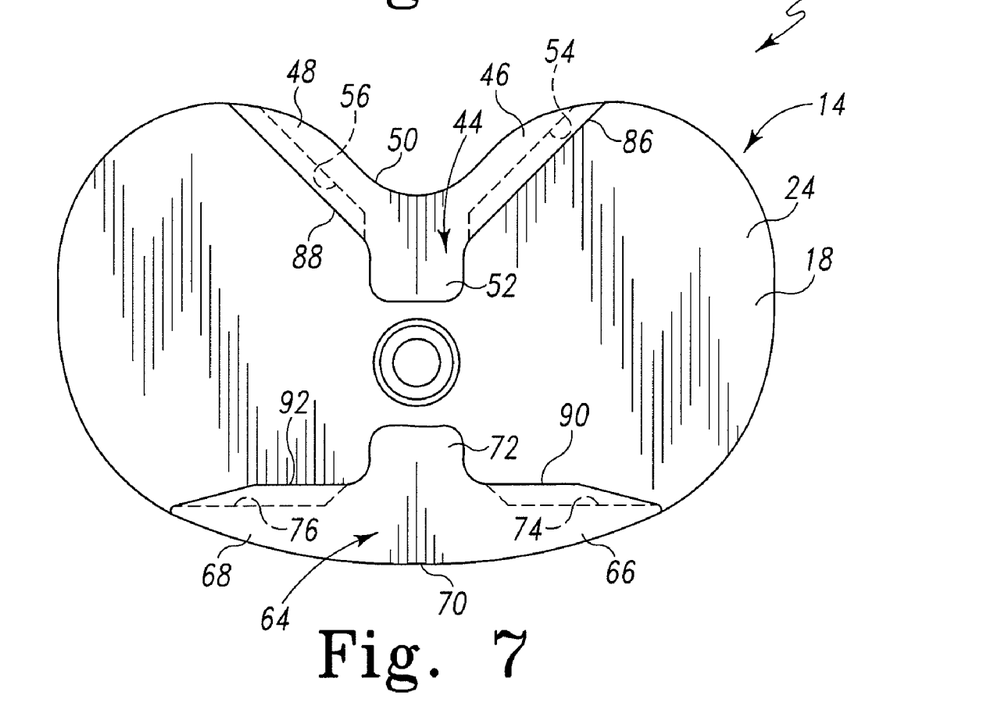

As shown in the illustrative embodiment of FIG. 7, the third arm 52 of the posterior buttress 44 is not contiguous with the third arm 72 of the anterior buttress 64. In other words, there is a gap between the arms 52, 72. It should be appreciated that the recesses 78, 80 defined in the lower surface 36 of the bearing 16 are likewise reshaped in the embodiment of FIG. 7 to accommodate the different shape of the buttresses 44, 64 of the tibial tray 14. In other words, the design of the recesses 78, 80 is altered to compliment the configuration of the separated buttresses 44, 64. It is also contemplated that the general configuration of the separated buttresses 44, 64 of FIG. 7, along with the corresponding configuration of the recesses 78, 80 and tabs 40, 42 of the complimentary bearing 16, may also remain the same across a range of differently-sized trays 14 and bearings 16 to accommodate the interchangeability of various sizes of trays and bearings in a similar manner to as described above in regard to FIG. 5.

Figure 8:
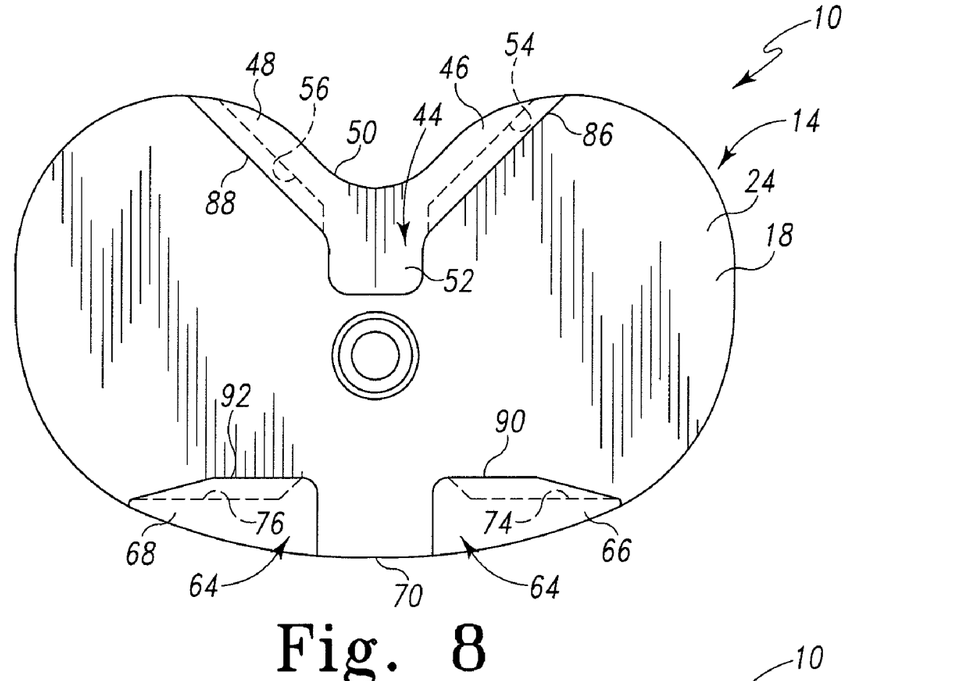

Turning to the embodiment of FIG. 8, the anterior buttress 64 is configured without the third arm 72. Moreover, the lateral arm 66 of the anterior buttress is spaced apart from the medial arm 68—i.e., there is a gap between the arms 66, 68. It should be appreciated that the recesses 78, 80 defined in the lower surface 36 of the bearing 16 are likewise reshaped in the embodiment of FIG. 8 to accommodate the different shape of the buttresses 44, 64 of the tibial tray 14. In other words, the design of the recesses 78, 80 is altered to compliment the configuration of the buttresses 44, 64. It is also contemplated that the general configuration of the buttresses 44, 64 of FIG. 8, along with the corresponding configuration of the recesses 78, 80 and tabs 40, 42 of the complimentary bearing 16, may also remain the same across a range of differently-sized trays 14 and bearings 16 to accommodate the interchangeability of various sizes of trays and bearings in a similar manner to as described above in regard to FIG. 5.

Figure 9:
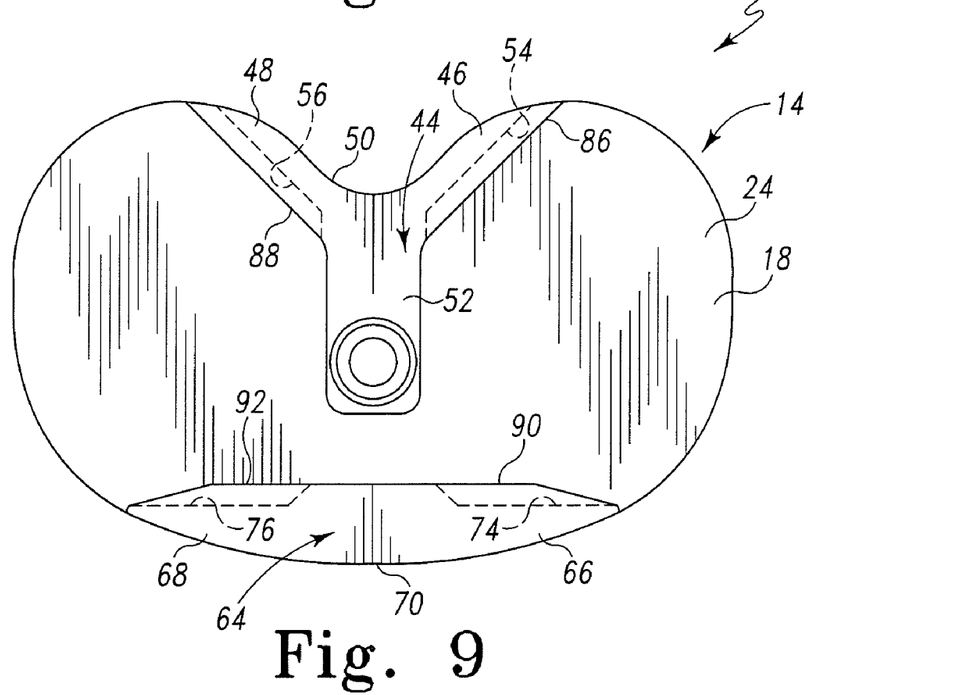

Yet another embodiment of the knee prosthesis 10 is shown in FIG. 9. Like the embodiment of FIG. 8, the anterior buttress 64 is configured without the third arm 72. However, unlike the design of FIG. 8, the lateral arm 66 of the anterior buttress is not spaced apart from the medial arm 68, but rather is contiguous therewith. Moreover, the third arm 52 of the posterior buttress 44 is longer than that of the embodiment shown in FIG. 8. As with the other embodiments described herein, it should be appreciated that the recesses 78, 80 defined in the lower surface 36 of the bearing 16 are likewise reshaped in the embodiment of FIG. 9 to accommodate the different shape of the buttresses 44, 64 of the tibial tray 14. In other words, the design of the recesses 78, 80 is altered to compliment the configuration of the buttresses 44, 64. It is also contemplated that the general configuration of the buttresses 44, 64 of FIG. 9, along with the corresponding configuration of the recesses 78, 80 and tabs 40, 42 of the complimentary bearing 16, may also remain the same across a range of differently-sized trays 14 and bearings 16 to accommodate the interchangeability of various sizes of trays and bearings in a similar manner to as described above in regard to FIG. 5.

As described herein, the various designs of the knee prosthesis 10 allow for the enhanced interchangeability of differently-sized components. In particular, any one of a plurality of differently-sized bearings may be secured to any one of a plurality of differently-sized tibial trays. As a result, articulation surface geometries and other features of the bearing may be enhanced for each size of femoral component. Such interchangeability also allows for smaller size increments in the design of a range of femoral components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. A fixed-bearing knee prosthesis, comprising:
a femoral component having a medial condyle surface and a lateral condyle surface,
a bearing having (i) a medial bearing surface configured to articulate with the medial condyle surface of the femoral component, and (ii) a lateral bearing surface configured to articulate with the lateral condyle surface of the femoral component, and
a tibial tray secured to the bearing, the tibial tray having a platform with a fixation member extending downwardly from a lower surface thereof, the platform having (i) a posterior buttress extending along a posterior section of a perimeter of the platform and extending upwardly from an upper surface of the platform, and (ii) an anterior buttress extending along an anterior section of the perimeter of the platform and extending upwardly from the upper surface of the platform,
wherein the anterior buttress has (i) a first arm extending along an anterior edge of the platform, (ii) a second arm extending along the anterior edge of the platform in a direction away from the first arm of the anterior buttress, and (iii) an undercut defined therein,
wherein the posterior buttress is generally Y-shaped and has (i) a first arm extending along a posterior edge of the platform and having a first undercut defined therein, (ii) a second arm extending along the posterior edge of the platform in a direction away from the first arm and having a second undercut defined therein, and (iii) a third arm extending anteriorly away from the first arm and the second arm, and
wherein (i) a first imaginary line extends along a lateral-most edge of the first arm, of the posterior buttress, (ii) a second imaginary line extends along a medial-most edge of the second arm of the posterior buttress and intersects the first imaginary line to define an angle of intersection therebetween, and (iii) the angle of intersection is between 45-145°.

2. The knee prosthesis of claim 1, wherein the angle of intersection is approximately 60-120°.

3. The knee prosthesis of claim 1, wherein the angle of intersection is approximately 90°.

4. The knee prosthesis of claim 1, wherein the anterior buttress is generally T-shaped and has:
a third arm extending posteriorly away from the first arm and the second arm, and
the undercut defined in the anterior buttress includes a first undercut defined in the first arm and a second undercut defined in the second arm.

5. The knee prosthesis of claim 4, wherein the third arm of the posterior buttress is contiguous with the third arm of the anterior buttress.

6. The knee prosthesis of claim 4, wherein the bearing includes:
a first posterior tab positioned in the first undercut defined in the first arm of the posterior buttress,
a second posterior tab positioned in the second undercut defined in the second arm of the posterior buttress,
a first anterior tab positioned in the first undercut defined in the first arm of the anterior buttress, and
a second anterior tab positioned in the second undercut defined in the second arm of the anterior buttress.

7. The knee prosthesis of claim 1, wherein the bearing includes:
a first posterior tab positioned in the first undercut defined in the first arm of the posterior buttress, and
a second posterior tab positioned in the second undercut defined in the second arm of the posterior buttress.

8. The knee prosthesis of claim 1, wherein:
the bearing has an upper surface and a lower surface,
both the medial bearing surface and the lateral bearing surface are defined in the upper surface of the bearing,
the lower surface of the bearing contacts the upper surface of the platform,
the lower surface of the platform has a posterior recess and an anterior recess formed therein, and the posterior buttress is positioned in the posterior recess and the anterior buttress is positioned in the anterior recess.

9. The knee prosthesis of claim 8, wherein:
the posterior buttress is contiguous with the anterior buttress, and
the posterior recess is contiguous with the anterior recess.

10. A fixed-bearing knee prosthesis, comprising:
a femoral component having a medial condyle surface and a lateral condyle surface,
a bearing having (i) a medial bearing surface configured to articulate with the medial condyle surface of the femoral component, and (ii) a lateral bearing surface configured to articulate with the lateral condyle surface of the femoral component, and
a tibial tray secured to the bearing, the tibial tray having a platform with a fixation member extending downwardly from a lower surface thereof, the platform having (i) a posterior buttress extending along a posterior section of a perimeter of the platform and extending upwardly from an upper surface of the platform, and (ii) an anterior buttress extending along an anterior section of the perimeter of the platform and extending upwardly from the upper surface of the platform,
wherein the posterior buttress is generally Y-shaped and has (i) a first arm extending along a posterior edge of the platform and having a first undercut defined therein, (ii) a second arm extending along the posterior edge of the platform in a direction away from the first arm and having a second undercut defined therein, and (iii) a third arm extending anteriorly away from the first arm and the second arm,
wherein the anterior buttress includes (i) a first arm extending along an anterior edge of the platform and having a first undercut defined therein, (ii) a second arm extending along the anterior edge of the platform in a direction away from the first arm of the anterior buttress and having a second undercut defined therein, and
a first imaginary line extends along a posterior-most edge of the first arm of the anterior buttress and a posterior-most edge of the second arm of the anterior buttress, (ii) a second imaginary line extends along the longitudinal axis of the third arm of the posterior buttress and intersects the first imaginary line to define an angle of intersection therebetween, and (iii) the angle of intersection is approximately 90°.

11. The knee prosthesis of claim 10, wherein the anterior buttress has a third arm extending posteriorly away from the first arm and the second arm in a direction parallel to the second imaginary line.

12. The knee prosthesis of claim 11, wherein the third arm of the posterior buttress is contiguous with the third arm of the anterior buttress.

13. The knee prosthesis of claim 10, wherein the bearing includes:
a first posterior tab positioned in the first undercut defined in the first arm of the posterior buttress,
a second posterior tab positioned in the second undercut defined in the second arm of the posterior buttress,
a first anterior tab positioned in the first undercut defined in the first arm of the anterior buttress, and
a second anterior tab positioned in the second undercut defined in the second arm of the anterior buttress.

14. The knee prosthesis of claim 10, wherein:
the bearing has an upper surface and a lower surface,
both the medial bearing surface and the lateral bearing surface are defined in the upper surface of the bearing,
the lower surface of the bearing contacts the upper surface of the platform,
the lower surface of the platform has a posterior recess and an anterior recess formed therein, and
the posterior buttress is positioned in the posterior recess and the anterior buttress is positioned in the anterior recess.

15. The knee prosthesis of claim 14, wherein:
the posterior recess is bounded by a posterior sidewall,
the posterior sidewall contacts the posterior buttress,
the anterior recess is bounded by an anterior sidewall, and
the anterior sidewall contacts the anterior buttress.

16. The knee prosthesis of claim 14, wherein:
the posterior buttress is contiguous with the anterior buttress, and
the posterior recess is contiguous with the anterior recess.

17. A fixed-bearing knee prosthesis, comprising:
a femoral component having a medial condyle surface and a lateral condyle surface,
a tibial tray having a platform with a fixation member extending downwardly from a lower surface thereof, the platform having (i) a generally Y-shaped posterior buttress extending upwardly from an upper surface of the platform and having a pair of arms extending along a posterior section of a perimeter of the platform, each of the pair of arms having an undercut defined therein, and (ii) an anterior buttress extending along an anterior section of the perimeter of the platform and extending upwardly from the upper surface of the platform, the anterior buttress having an undercut defined therein, and
a plurality of bearings configured to be separately secured to the tibial tray, wherein each of the plurality of bearings has (i) a width that is different from at least some of the other of the plurality of bearings, (ii) an upper surface having a medial bearing surface configured to articulate with the medial condyle surface of the femoral component and a lateral bearing surface configured to articulate with the lateral condyle surface of the femoral component, (iii) a lower surface having at least one recess defined therein to receive the posterior buttress and the anterior buttress, and (iv) a pair of posterior locking tabs arranged to be respectively received in the undercuts defined in each of the pair of arms of the posterior buttress.

18. The knee prosthesis of claim 17, wherein the at least one recess of the bearing defines a single, contiguous recess that receives both the posterior buttress and the anterior buttress.

19. The knee prosthesis of claim 17, wherein:
the anterior buttress is generally T-shaped and has a pair of arms extending along an anterior edge of the platform,
the undercut of the anterior buttress comprises two undercuts one of which is defined in each arm of the pair of arms of the anterior buttress, and
each of the plurality of bearings further includes a pair of anterior locking tabs arranged to be respectively received in the undercuts defined in each of the pair of arms of the anterior buttress.

20. The knee prosthesis of claim 17, wherein the posterior buttress is contiguous with the anterior buttress.

* * * * *